United States Patent [19]
Ajioka et al.

[11] Patent Number: 5,206,413
[45] Date of Patent: Apr. 27, 1993

[54] METHOD FOR PREPARING α-L-ASPARTYL-L-PHENYLALANINE METHYL ESTER

[75] Inventors: Masanobu Ajioka, Yokohama; Takeshi Oura, Zushi; Chojiro Higuchi, Kamakura; Toshio Katoh, Kawasaki; Akihiro Yamaguchi, Kamakura, all of Japan

[73] Assignee: Mitsui Toatsu Chemicals, Incorporated, Tokyo, Japan

[21] Appl. No.: 537,451

[22] Filed: Jun. 14, 1990

[30] Foreign Application Priority Data

Jun. 14, 1989 [JP] Japan ................................. 1-149515

[51] Int. Cl.$^5$ ..................... C07C 229/00; A61K 37/00
[52] U.S. Cl. ...................................... 560/41; 562/445; 562/571
[58] Field of Search .................. 560/41; 562/445, 571; 514/19

[56] References Cited

U.S. PATENT DOCUMENTS 3,833,554  9/1974  Ariyoshi et al. ...................... 560/41
4,309,341  1/1982  Kubo et al. .......................... 560/41

Primary Examiner—Robert A. Wax
Assistant Examiner—Richard C. Ekstrom
Attorney, Agent, or Firm—Millen, White, Zelano & Branigan

[57] ABSTRACT

A method for preparing α-L-aspartyl-L-phenylalanine methyl ester (α-APM), substantially free from acid ion contamination, is disclosed which comprises the steps of contacting a solution of a mineral acid salt or an organic sulfonic acid salt of α-APM in an aqueous solvent with an anion exchange resin in free base form, separating the resin from the thus-produced solution of α-APM; and isolating the α-APM therefrom, preferably with regeneration and recycling the resin.

9 Claims, No Drawings

METHOD FOR PREPARING α-L-ASPARTYL-L-PHENYLALANINE METHYL ESTER

BACKGROUND OF THE INVENTION (a) Field of the Invention

The present invention relates to a method for preparing α-L-aspartyl-L-phenylalanine methyl ester from an acid addition salt thereof.

α-L-aspartyl-L-phenylalanine methyl ester (hereinafter abbreviated as "α-APM") is a widely known dipeptide sweetener. It has sweetness of good quality and a high degree of sweetness, i.e., about 200 times the sweetness of sucrose. The demand for α-APM as a diet sweetener is rapidly expanding.

(b) Description of the Prior Art

α-APM is a dipeptide composed of L-aspartic acid and L-phenylalanine methyl ester. The known methods for the preparation of α-APM can be classified into a biochemical process utilizing microorganisms and a chemical process. For each process, various methods have been disclosed.

In the biochemical process, N-benzyloxycarbonyl-L-aspartic acid and L-phenylakanien methyl ester are condensed in the presence of metalloprotease to obtain N-benzyloxycarbonyl-α-L-aspartyl-L-phenylalanine methyl ester. The benzyloxycarbonyl group is then removed from the intermediate by catalytic reduction to give α-APM (Japanese Laid-open Patent Publication No. 55-135595).

As a typical example of the chemical process, L-aspartic anhydride having a protected amino group is subjected to a condensation reaction with L-phenylalanine methyl ester in a suitable solvent, and the protective group is then removed therefrom by a conventional method to obtain α-APM (U.S. Pat. No. 3,786,039).

In another method, N-formyl-L-aspartic anhydride and L-phenylalanine are condensed, and deformylation and esterification are then simultaneously carried out in an acidic medium (Japanese Laid-open Patent Publication No. 53-82752).

When an N-protected-L-aspartic anhydride is used as a starting material, β-L-aspartyl-L-phenylalanine methyl ester (hereinafter abbreviated as "β-APM") is inevitably formed as a by-product in addition to α-APM. This β-APM has no sweetening effect and instead has a bitter taste, and so it is necessary to remove the β-APM from the thus-produced α-APM.

In every purification method, removal not only of β-APM but also other impurities from α-APM is required.

Japanese Patent Publication No. 49-41425 discloses the technique of purifying crude α-APM containing β-APM as a salt of a hydrohalogenic acid from an aqueous solution.

Furthermore, Japanese Patent Publication No. 51-40071 discloses a process of obtaining high-purity α-APM which comprises dissolving crude α-APM containing impurities in an aqueous mineral acid solution, removing 5-benzyl-3,6-dioxo-2-piperazine acetic acid (hereinafter abbreviated as "DKP") which is a reaction by-product, and then effecting neutralization.

In these methods, in order to isolate α-APM from the reaction solvent or to separate impurities such as β-APM and DKP, a mineral acid salt or an organic sulfonate of α-APM is formed and then neutralized with a base.

Usually, when isolating α-APM by neutralizing an acid addition salt of α-APM, the neutralization is carried out with a neutralizing agent such as an inorganic base, e.g., sodium hydroxide, or an organic base, e.g., triethylamine, in an aqueous solution, and the precipitated α-APM crystals are then isolated by filtration. As the acid component of a mineral acid salt or the organic sulfonic acid salt of α-APM, hydrochloric acid, sulfuric acid or p-toluene sulfonic acid is usually used. Therefore, when this salt is neutralized with the inorganic or organic base, at least an equilmolar inorganic or organic salt is present in the mother liquor, and this salt adheres to a filter cake and contaminates the resulting product. The contamination of the product with a salt such as hydrochloride or a sulfate reduces the commercial value of the product. According to the standard specification of usual amino acids, the content of anions such as chlorine ions and sulfate ions should be controlled to a level of 0.02 or 0.03%.

In addition, in this neutralization reaction, dissolved α-APM is present in a perceptible amount in the filtrate, which is why the yield is low. The filtrate can be reused as the solvent for the neutralization reaction, but in this case, the contained salt of a mineral acid or an organic sulfonic acid therein is accumulates in the solvent, with the result that the amount of the salt in the isolated product increases. Accordingly, a purification operation is necessary to remove the inorganic ions from the filtered and isolated α-APM.

Since the solubility of α-APM in a solvent such as water is low, a large amount of the solvent is required when α-APM is completely dissolved and then treated. In addition, being unstable to heat, α-APM cannot be treated at a high temperature for a long period of time. Conversely, when α-APM is treated in a suspension state, the properties of its slurry are so bad that operation such as stirring or liquid transfer is very difficult, and if the stirring is carried out at a high speed, bubbles which are hard to break are formed. Moreover, if a filtration speed is slow, the resulting cake inconveniently contains a large amount of the liquid. Thus, it is industrially very inefficient that the purification operation is repeated in which an α-APM solution or suspension having the bad operation characteristics is employed.

Furthermore, in the usual neutralization reaction using a soluble base, contact of α-APM with the base results in the formation of DKP, which deteriorates the yield, and if the product is contaminated with the formed DKP, the commercial value of the product is reduced.

As discussed above, in the conventional neutralization process for the acid salt of α-APM, the yield is low, and a repurification operation is necessary. Consequently, the above-mentioned process is industrially undesirable.

SUMMARY OF THE INVENTION

An object of the present invention is to provide a method for producing α-L-aspartyl-L-phenylalanine methyl ester (α-APM) from an acid addition salt thereof, substantially free from the anion of the acid addition salt.

This object can be achieved by contacting an aqueous solution of an acid addition salt, e.g., a mineral acid salt or an organic sulfonic acid salt of α-L-aspartyl-L- phenylalanine methyl ester with an OH type anion exchange resin in free base form and isolating the α-APM from the thus-obtained solution thereof.

This method is industrially excellent, because a neutralization operation is easy, the formation of by-products during the neutralization treatment and a treatment loss are inhibited, and after the treatment, further repurification of the thus-produced α-APM is unnecessary.

DETAILED DESCRIPTION OF THE INVENTION

The present inventors have intensively researched with the intention of solving the problems of the above-mentioned preparation methods, and as a result they have found that when an acid addition salt, e.g., a mineral acid salt or an organic sulfonic acid salt of α-APM is dissolved in an aqueous solvent and then neutralized with an OH type ion exchange resin, surprisingly, the anions of the acid forming the salt of the α-APM are selectively adsorbed on the resin and α-APM is not adsorbed on the resin, so that an aqueous solution containing α-APM alone is obtained. The present invention has been completed on the basis of this knowledge.

α-APM is in cation form when acidic, in a non-charged form of a paired ion when neutral, and in the form of an anion when alkaline. Thus, α-APM is not adsorbed by the anion exchange resin when the aqueous solution containing it is neutral or acidic.

When a mineral acid or organic, e.g., sulfonic acid salt of α-APM is dissolved in a neutral aqueous solvent, the solution becomes weakly acidic, i.e., it has a pH between about 1 and 7. When the resulting solution is brought into contact with the anion exchange resin, only the acid anion is adsorbed thereon, and α-APM is not adsorbed. However, any DKP in the solution is adsorbed on the anion exchange resin and thus is separated from the α-APM.

In the present invention, the mineral acid, organic sulfonic acid or like salt of α-APM prepared by various methods can be used. Examples of the acid salts used in the present invention include the hydrochloride, sulfate, phosphate, nitrate, methanesulfonate ethanesulfonate, benzenesulfonate and p-toluenesulfonate salts.

The starting α-APM salt can be substantially pure, e.g., 90% or purer. However, a starting purity of at least about 95% is preferred as an object of the invention to produce substantially pure, e.g., food grade, α-APM.

The anion exchange resin used in the method of the present invention which may be of the weak base or strong base type, is used in free base form. Since they inhibit the formation of DKP, the weak base ion exchange resin is particularly preferred. The substrate of the ion exchange resin can be any type such as a gel type, a porous type or a macroporous type. Therefore, any weakly or strongly basic anion exchange resin can be used without any restriction.

For a description of such ion exchange resins, see Mcgraw Hill Series in Advanced Chemistry, Ion Exchange, pages 47–58 and 580, whose disclosure is incorporated herein by reference.

The amount of the ion exchange resin employed is 0.5 chemical equivalents or more, preferably 1 to 10 equivalents in terms of its ion exchange capacity in its wet state with respect to the chemical equivalent amount of the mineral acid or the organic acid, e.g., sulfonic acid, contained in the starting α-APM acid addition salt. When the amount of the ion exchange resin is less than 1 equivalent, a portion of the α-APM remains in salt form but it is possible to decrease the amount thereof contained in the α-APM in a subsequent isolation operation, such as filtration or washing. When the amount of the resin is less than 0.5 equivalent, the amount of the anion which must be removed in a subsequent operation is too much and the industrial advantage of the method of the present invention cannot be obtained. Conversely, it is not economical to use more than 10 equivalents of the resin, because the amount of α-APM which is retained in the resin increases undesirably, so that the increased amount of α-APM is eventually lost. Taking the formation of DKP into consideration, the amount of the ion exchange resin is more preferably from 0.8 to 1.5 equivalents.

The ion exchange reaction is effected at a temperature up to 70° C., preferably from 20° to 60° C., more preferably above room temperature, e.g., 40°–60° C. When the temperature is higher than 70° C., α-APM decomposes to form α-L-aspartyl-L-phenylalanine and DKP, which produces a drop in the yield. When the temperature of the neutralization reaction is too low, the starting α-APM salt must be used at a low concentration, because the solubility of α-APM at low temperatures is low. When such a low concentration is used, the volumetric efficiency of the process deteriorates.

The ion exchange reaction of the present invention is conducted in an aqueous medium, i.e., in an aqueous solution or a solvent comprising water and a water-miscible organic solvent. The water-miscible organic solvents includes alcohols such as methanol, ethanol, n-propanol, isopropanol, tert-butanol, cellosolve and methyl cellosolve, acetone, dioxane, tetrahydrofuran, N,N-dimethylformamide, N,N-diethylformamide and dimethyl sulfoxide. When a mixture of water and an organic solvent are used, the ratio between water and the organic solvent can be optionally selected.

The starting acid addition salt forms an acidic solution in the aqueous solvent. Although additional acid can be present therein, the amount thereof should be limited because it competes with the anion of the acid addition salt of α-APM and reduces the ion exchange capacity of the resin.

There is no particular limit on the amount of solvent employed, except it is necessary that the starting α-APM salt and the thus-produced α-APM remain dissolved therein at the selected reaction temperature. When water is used, a weight amount from about 20 to 100 times, preferably 25 to 50 times, that of the starting α-APM salt is usually employed.

In the practice of the method of the present invention batch-wise, the anion exchange resin is added to the α-APM acid addition, e.g., mineral acid salt or organic sulfonic acid salt solution in accordance, followed by stirring, in order to carry out the ion exchange reaction. The resin is then removed therefrom by filtration, whereby an α-APM solution is obtained. Alternatively, the α-APM acid addition salt solution is allowed to flow through a column packed with the ion exchange resin and an α-APM solution which flows therefrom is collected. The thus obtained α-APM solution is then evaporated to dryness or, alternatively, it is cooled or concentrated to deposit crystals of the α-APM and the latter may be then isolated by a usual solid-liquid separation technique.

The resin used for the ion exchange reaction can be regenerated in the usual manner using an aqueous alkali hydroxide solution so as to form the (free base form) OH type, which can be reused.

In the method of the present invention, the anion content in the α-APM solution obtained by the neutralization is low, and so the amount of the anion which adheres to the α-APM solid isolated therefrom is also small. Therefore, in a subsequent step, α-APM with low anion content can be isolated without employing any especial purifiation technique.

The present invention will now be described in detail in reference to examples.

In the examples, α-APM was analyzed by means of HLC, and chlorine ions were measured by a potentiometric titration method using a silver nitrate solution.

EXAMPLE 1

To 1,103.3 g of an aqueous solution containing 33.1 g of α-APM hydrochloride was added 167 ml of the free base form of a weak base OH type anion exchange resin (Lewatit MP-62 made by Bayer AG) which is a weak base, microporous type anion exchange resin having tertiary amine group as an ion exchangeable group. The mixture was then stirred at 55° C. for 30 minutes. The resin was removed from the system by hot filtration, and the resin was then washed twice with 167 ml of warm water at 55° C. The filtrate was mixed with the wash liquid in order to obtain 1,086 g of a solution, which contained 25.9 g of α-APM (yield 88.2%) and 240 ppm of chlorine ions.

The solution was cooled to 5° C., and the deposited crystals were filtered and dried to obtain 20.2 g of α-APM. The total yield was 68.6%, and a chlorine content in the crystals was 0.03%.

Under reduced pressure, 1,038 g of the filtrate obtained in the filtration step was concentrated at 40° C. to 725 g and 26.6 g of fresh α-APM hydrochloride was dissolved therein. To this solution was added 167 ml of the weak base OH type anion exchange resin, and the mixture was then stirred at 55° C. for 30 minutes. The resin was removed from the system by hot filtration and then washed twice with 167 ml of warm water at 55° C. Afterward, the thus-obtained filtrate, after mixing the wash liquid, contained 26.1 g of α-APM and 230 ppm of chlorine ions.

The solution was cooled to 5° C., and the precipitated crystals were filtered and dried to obtain 20.5 g of α-APM with a chlorine content of 0.03%. The total yield to the freshly fed α-APM was 86.5%.

EXAMPLE 2

The same procedure as in Example 1 was employed except that the free base form of water-containing resin was used which was regenerated by immersing 188 ml of a strong base anion exchange resin in Cl salt form (Lewatit MP-500 made by Bayer AG), which is strong base macroporous type anion exchange resin with quartenary amine group as ion exchangeable group, in an aqueous sodium hydroxide solution and then thoroughly washing the same with water. 1,084 g of a solution was obtained which contained 25.4 g of α-APM (yield 86.4%) and the concentration of chlorine ions therein was 92 ppm.

The solution was cooled to 5° C., and the deposited crystals were filtered and dried to obtain 18.2 g of α-APM with a chlorine content of 0.01%. The total yield was 61.9%.

As in Example 1, the resulting filtrate was concentrated to 725 g, and 25.0 g of fresh α-APM hdyrochloride was added thereto. To this solution was added the OH type water-containing resin produced by immersing 188 ml of a strong base Cl type anion exchange resin in an aqueous sodium hydroxide solution and then thoroughly washing the same with water. The obtained filtrate was mixed with the wash liquid to obtain a solution which contained 25.7 g of α-APM and 230 ppm chlorine ions.

The solution was then cooled to 5° C., and the deposited crystals were filtered and dried to obtain 18.5 g of α-APM with a chlorine content of 0.01%. The total yield to the freshly fed α-APM was 83.3%.

COMPARATIVE EXAMPLE 1

To 725.0 g of an aqueous solution containing 33.1 g of α-APM hydrochloride was added dropwise with stirring 6.1 g of 28% aqueous ammonia so as to adjust the pH to 5.0. The deposited crystals were filtered to obtain 59.8 g of a filter cake containing 25.1 g of α-APM (yield 85.1%) with a chlorine content of 0.3%.

The filter cake was then dispersed in 567.7 g of water and the resulting dispersion was stirred at 25° C. for 1 hour and then cooled to 5° C. to deposit crystals. The latter were collected by filtration and then dried to obtain 21.6 g of α-APM with a chlorine content of 0.04%. The yield was 76.5%.

EXAMPLE 3

735.7 g of an aqueous solution containing 33.1 g of α-APM hydrochloride was allowed to flow through a column with a heated jacket and packed with 60 ml of a weak base OH type anion exchange resin (Lewatit MP-62 made by Bayer AG) at a flow rate of 5 cm/minute, while the temperature of the column was maintained at 55° C., followed by water until 1,300 ml of effluent was collected. This solution, contained 26.8 g of α-APM (yield 91.2%) and 100 ppm of chlorine ions.

The solution was cooled to 5° C., and the deposited crystals were filtered and dried to obtain 19.7 g of e-APM with a chlorine content of 0.01%. The total yield was 67.0%.

The resin in the used column was regenerated in free base form with 1N aqueous sodium hydroxide solution and then thoroughly washed with water. A solution was prepared by dissolving 25.1 g of additional α-APM hydrochloride in the concentrate obtained by concentrating 1,251.3 g of the filtrate of the filtration step at 40° C. under reduced pressure to 750 g. The solution was flowed through the regenerated column at 55° C. at a flow rate of 3 cm/minute, followed by water until 1,300 ml of effluent was collected. This solution contained 26.6 g of α-APM and 120 ppm of chlorine ions.

The solution was cooled to 5° C., and the deposited crystals were filtered and dried to obtain 19.5 g of α-APM with a chlorine content of 0.01%. The total yield based on the additional α-APM was 92.9%.

EXAMPLES 4 TO 7

The same procedure as in Example 3 was employed except that the salts of α-APM shown in Table 1 were employed. The results are set forth in Table 1.

TABLE 1

| | Example No. | | | |
|---|---|---|---|---|
| | 4 | 5 | 6 | 7 |
| | | Acid | | |
| | Sulfuric Acid | Nitric Acid | Phosphoric Acid | PTS |
| First Time | | | | |
| Amount of APM Salt (g) | 39.2 | 35.7 | 39.2 | 46.6 |
| Effluent | | | | |
| α-APM (g) | 27.2 | 27.0 | 26.6 | 26.8 |
| Yield (%) | 92.6 | 91.8 | 90.4 | 91.3 |
| Anion (ppm) | 70 | 90 | 80 | 130 |
| Isolated α-APM | | | | |
| Yield (g) | 18.6 | 18.3 | 18.4 | 18.8 |
| Yield (%) | 63.1 | 62.3 | 62.7 | 63.8 |
| Anion (%) | 0.01 | 0.01 | 0.01 | 0.02 |
| Second Time | | | | |
| Freshly Fed α-APM Salt (g) | 29.7 | 25.1 | 28.3 | 33.9 |
| Effluent | | | | |
| α-APM (g) | 25.8 | 26.5 | 25.9 | 26.2 |
| Anion (ppm) | 60 | 80 | 80 | 130 |
| Isolated α-APM | | | | |
| Yield (g) | 18.4 | 18.0 | 18.0 | 18.6 |
| Yield (%) | 88.5 | 87.0 | 84.9 | 86.9 |
| Anion (%) | 0.01 | 0.01 | 0.01 | 0.02 |

PTS: p-Toluenesulfonic acid

EXAMPLE 8

980.0 g of an aqueous solution containing 33.1 g of α-APM hydrochloride and 0.7 g of free hydrochloric acid was allowed to flow through a column with a heated jacket and packed with an OH type water-containing resin, regenerated in free base form by immersing 120 ml of a strong base Cl type anion exchange resin (Lewatit MP-500 made by Bayer AG) in an aqueous sodium hydroxide solution and then thoroughly washing the same with water, at a flow rate of 10 cm/minute, while the temperature of the column was maintained at 45° C., followed by water until 1,300 ml of effluent was collected. This solution, contained 26.9 g of α-APM (yield 89.2%) and 30 ppm of chlorine ions.

The solution was cooled to 5° C., and the deposited crystals were filtered and dried to obtain 18.8 g of α-APM with a chlorine content of 0.01% or less. The total yield was 63.9%.

The resin in the used column was regenerated in free base form with a 1N aqueous sodium hydroxide solution and then thoroughly washed with water. A solution prepared by dissolving 23.9 g of additional α-APM hydrochloride in a concentrate obtained by concentrating 1,258.2 g of the filtrate of the filtration step at 40° C. under reduced pressure to 950 g was allowed to flow through the regenerated resin column at 55° C. at a flow rate of 3 cm/minute, followed by water until 1,300 ml of effluent was collected. This solution contained 27.2 g of α-APM and 40 ppm of chlorine ions.

The solution was cooled to 5° C., and the deposited crystals were filtered and dried to obtain 19.1 g of α-APM with a chlorine content of 0.01% or less. The total yield based on the additional α-APM was 89.7%.

EXAMPLE 9

420.0 g of a 50% aqueous methanol solution containing 33.1 g of α-APM hydrochloride and 0.7 g of free hydrochloric acid was allowed to flow through a column with a heated jacket and packed with an OH type water-containing resin, regenerated in free base form by immersing 133 ml of a weak base anion exchange resin in Cl salt form (Lewatit MP-62 made by Bayer AG) in an aqueous sodium hydroxide solution and then thoroughly washing the same with water and then 50% aqueous methanol, at a flow rate of 5 cm/minute, while the temperature of the column was maintained at 55° C., followed by 50% aqueous methanol, until 800 ml of effluent was collected. This solution contained 26.5 g of α-APM (yield 90.3%) and 80 ppm of chlorine ions.

The solution was cooled to 5° C., and the deposited crystals were filtered and dried to obtain 22.0 g of α-APM with chlorine content of 0.01%. The total yield was 74.9%.

The resin in the used column was regenerated in free base form with a 1N aqueous sodium hydroxide solution and then thoroughly washed with water. A solution prepared by dissolving 28.0 g of additional α-APM hydrochloride in 751.1 g of the filtrate obtained in the filtration step was allowed to flow through the regenerated column at 55° C. at a flow rate of 3 cm/minute, followed by water until 1,300 ml of effluent was collected. This solution contained 26.6 g of α-APM and 70 ppm of chlorine ions.

The solution was cooled to 5° C., and the deposited crystals were filtered and dried to obtain 21.8 g of α-APM with a chlorine content of 0.01%. The total yield based on the additional α-APM was 89.0%.

EXAMPLE 10

The same procedure as in Example 9 was employed except that the solvent was 50% aqueous ethanol to obtain 800 ml of solution containing 26.1 g of α-APM (yield 88.8%) and 70 ppm of chlorine ions.

The solution was cooled to 5° C., and the deposited crystals were filtered and dried to obtain 20.4 g of α-APM with a chlorine content of 0.01%. The total yield was 69.5%.

The resin in the used column was regenerated into free base form of an OH type with a 1N aqueous sodium hydroxide solution and then thoroughly washed with water. A solution prepared by dissolving 26.6 g of additional α-APM hydrochloride in 754.7 g of the filtrate obtained in the filtration step was allowed to flow through the regenerated column at 55° C. at a flow rate of 3 cm/minute, followed by water until 1,300 ml of effluent was collected. This solution contained 26.5 g of α-APM and 70 ppm of chlorine ions.

The solution was cooled to 5° C., and the deposited crystals were filtered and dried to obtain 20.2 g of α-APM with a chlorine content of 0.01%. The total yield based on the additional α-APM was 85.0%.

What is claimed is:

1. A method for converting substantially pure α-L-aspartyl-L-phenylalanine methyl ester (α-APM) in acid addition salt form to its free base form, substantially free from acid ion contamination, which comprises the steps of contacting a solution of a substantially pure acid addition salt of α-L-aspartyl-L-phenylalanine methyl ester in an aqueous solvent with an anion exchange resin in free base form, thereby producing an aqueous solution of substantially pure α-APM in free base form; separating the ion exchange resin therefrom; and then isolating therefrom α-APM substantially free from the acid anions of the acid addition salt.

2. The method of claim 1, wherein the anion exchange resin is a weak base type resin.

3. The method of claim 1, wherein the aqueous solvent is water or a mixture of methanol or ethanol and water.

4. The method of claim 1, wherein the acid addition salt is at least 95% pure and is a salt of a mineral acid.

5. The method of claim 4, wherein the acid addition salt is the hydrochloride.

6. The method of claim 1, wherein the contacting step is conducted at about 40° to 60° C.

7. The method of claim 1, further comprising cooling the thus obtained solution and separating the thus-precipitated α-APM.

8. The method of claim 1, wherein the contacted resin is regenerated with base and recycled with additional acid addition salt of α-APM dissolved in additional aqueous solvent or the aqueous solvent from which the α-APM was isolated.

9. The method of claim 1, wherein the anion exchange resin is a weak base type resin; wherein the aqueous solvent is water or a mixture of methanol or ethanol and water; wherein the acid addition salt is at least 95% pure and is the hydrochloride; wherein the contacting step is conducted at about 40° to 60° C.; and wherein the α-APM is separated by cooling the solution thereof; and wherein the contacted resin is regenerated with base and recycled with acid addition salt of α-APM dissolved in additional aqueous solvent or the aqueous solvent from which the α-APM was isolated.

* * * * *